United States Patent [19]
Bacus

[11] Patent Number: 5,218,645
[45] Date of Patent: Jun. 8, 1993

[54] METHOD AND APPARATUS FOR SEPARATING CELL OBJECTS FOR ANALYSIS

[75] Inventor: James V. Bacus, Lombard, Ill.

[73] Assignee: Cell Analysis Systems, Inc., Elmhurst, Ill.

[21] Appl. No.: 677,213

[22] Filed: Mar. 29, 1991

[51] Int. Cl.$^5$ .................................. G06K 9/00
[52] U.S. Cl. ................................. 382/6; 382/48; 364/413.08
[58] Field of Search ............ 382/6, 48; 364/413.08, 364/413.1; 358/107, 93; 356/39

[56] References Cited

U.S. PATENT DOCUMENTS

| | | | |
|---|---|---|---|
| 4,453,266 | 6/1984 | Bacus | 382/6 |
| 4,592,089 | 5/1986 | Hartman | 382/6 |
| 4,845,552 | 7/1989 | Jaggi et al. | 382/6 |
| 4,932,044 | 6/1990 | Williams et al. | 382/6 |
| 5,016,283 | 5/1991 | Bacus et al. | 364/413.08 |
| 5,031,099 | 7/1991 | Kettler | 364/413.08 |

OTHER PUBLICATIONS

G. Brugal, "Image Analysis of Microscopic Preparations", *Method and Achievements in Experimental Pathology*, vol. 11, pp. 1-33.

W. Auffermann et al., "Early Detection of Precancerous Lesions in Dysplasias of the Lung by Rapid DNA Image Cytometry", *Analyt. & Quanat. Cytology & Histology*, vol. 7, No. 3, Sep. 1985, pp. 218-226.

W. Aufferman et al., "Rapid Diagnostic DNA Cytometry with an Automatic Microscope and a TV Image-Analysis System", *Analyt. & Quant. Cytology & Histology*, vol. 6, No. 3, pp. 179-188.

*Primary Examiner*—Jose Couso
*Attorney, Agent, or Firm*—Fitch, Even, Tabin & Flannery

[57] ABSTRACT

A method and apparatus for analyzing the cell objects of a cell sample for the diagnosis and treatment of possible cancer is disclosed. An optical image of the cell sample is digitized and stored in a frame buffer. The digital image is then displayed on a video monitor. The apparatus can automatically select cell objects from the sample for analysis. Also, an operator can influence the selection of cell objects by manipulating a computer pointing device (mouse) to draw lines on the displayed image. When a line is drawn through a cell object, the cell object can be separated into portions for analysis. When a line is drawn around a region of interest in the image, the region of interest can be separately analyzed to the exclusion of the rest of the image.

11 Claims, 8 Drawing Sheets

| 3 | 2 | 1 |
|---|---|---|
| 4 | X | 0 |
| 5 | 6 | 7 |

FIG.18

METHOD AND APPARATUS FOR SEPARATING CELL OBJECTS FOR ANALYSIS

BACKGROUND OF THE INVENTION

The invention relates to a system for performing an analysis of a cell sample containing cell objects and particularly to such a system which enables operators of the system to influence the portion of the cell sample to be analyzed.

One of the problems which faces pathologists in their clinical practice is that of determining whether a cell sample taken from a patient during a biopsy procedure or the like is benign or malignant. Although a surgeon may have a good intuition about the type of tissue mass which he has removed, nevertheless he must confirm his preliminary diagnosis with a histological examination of the cell sample removed from the patient. The histological examination entails cell staining procedures which allow the morphological features of the cells to be seen relatively easily in a light microscope. A pathologist after having examined the stained cell sample, makes a qualitative determination of the state of the tissue or the patient from whom the sample was removed and reaches a conclusion as to whether the patient is normal or has a premalignant condition which might place him at risk of a malignancy in the future or has cancer. While this diagnostic method has provided some degree of predictability in the past, it is somewhat lacking in scientific rigor, since it is heavily reliant on the subjective judgment of the pathologist.

Systems have been designed which automate the cellular examination process. In U.S. Pat. No. 4,741,043 to Bacus for Method and Apparatus for Image Analyses of Biological Specimens, an automated method and a system for measuring the DNA of cell nuclei are disclosed which employ differential staining of the DNA in cell nuclei and image processing. Cell objects which comprise cell nuclei are automatically selected, the DNA mass of each nucleus is then measured and a histogram is generated to show the frequency of nuclei having particular DNA masses.

The system of the above-mentioned Bacus patent, digitizes an optical image of a cell sample and selects for analysis cell objects of interest by identifying continuous perimeters around the cell objects. For most cell objects in cell samples, this yields satisfactory results, however, in some instances, cell objects can be difficult for the apparatus to distinguish. For example, when two cell objects are abutting one another, they present an optical image which appears continuous and which has a single perimeter surrounding both objects. Such abutting cell objects may be interpreted by automated apparatus as a single cell object, resulting in slightly inaccurate results, particularly when a measured quantity is reported on a per cell object basis. Also the cell objects may be arranged in such a way that it is not possible for the apparatus to select certain desirable cell objects for analysis. This might occur when the gray scale values of the background and the cell objects and the background are similar and overlapping.

Automated methods of identifying the boundaries of objects in images are also described in "Digital Image Processing", Second Ed., 1987 by R. C. Gonzalez and P. Wintz and "Video Microscopy", 1986 by Shinya Inoue'.

In order to select and appropriately analyze cell objects of the difficult to distinguish type, a need exists for an apparatus which permits human operators to modify the apparent boundaries of cell objects in the cell sample image, and to thereby influence the selection of cell objects for analysis.

SUMMARY OF THE INVENTION

This need is met and a technical advance is achieved in accordance with the present invention in which an operator creates lines on a displayed video image of a cell sample which lines are used by cell object search routines as cell object boundaries or portions thereof. The lines created by the operator cause changes in stored digital representations of the image picture elements which changes are detected as boundary indications by the search routines. A method for analyzing a cell sample, including a cell object in accordance with the invention comprises storing image representing values in an array of storage locations, displaying an image of the sample to an operator which has the capability to change selected ones of the stored values to a unique value which is, by design, indicative of a cell object boundary. A search routine is then performed on the values stored in the storage locations to identify cell object boundaries. The search routine recognizes the unique value as a boundary identifying value. After the boundary is identified by the search routine, the region of the cell sample delimited by the boundary is analyzed by a predetermined cell object analysis routine. The predetermined cell object analysis routine can be a perimeter and area measuring routine, a DNA mass measuring routine or other routines for measuring cell object attributes.

Before the boundary search routine is performed, selected storage locations are assigned the unique value to permit the operator to influence the boundaries identified by the search routine. In the preferred embodiment, the operator selects storage locations to store the unique value by drawing a line on a video image of the cell sample and the apparatus stores the unique value in storage locations corresponding to the picture elements of the video image traversed by the line. Such line drawing by the operator permits the separation of a single cell object on the video image into two or more cell objects for analysis.

The present invention can also be used in a select segments mode to isolate a region of a cell sample for analysis. In the select segments mode, the operator draws a closed line on the video image around a region of interest. The storage locations corresponding to the video image picture elements traversed by the line are then set to the unique boundary value. A set segments search routine is performed on the storage locations. The select segment search routine identifies the boundary defined by the storage locations storing the unique value and an analysis routine can be performed on the region delimited by the identified boundary.

In the preferred embodiment, an optical image of the cell sample is produced and separated into a plurality of picture elements, each of which corresponds to one of the storage locations. The gray level value of each picture element is digitally encoded and stored in its corresponding storage location. At least one value of the range of digital values which can be stored in a storage location is reserved as a unique boundary indicating value. In order to clarify the image of the cell sample, the storage locations storing only values representing background around the cell object are set to a background indicating value such as zero. A displayed video image of the cell sample after the background adjustment consists of at least one cell object on a blank background.

The operator can then select a cut object mode of operation in which a computer pointing device such as a mouse or track ball is used to move a cursor on the displayed video image. The cursor draws a line through a cell object from image background to image background. Upon selecting the line, for example, by pressing a button on a mouse, the storage locations corresponding to picture elements traversed by the line are set to the reserved unique boundary value. After the line is selected, a boundary search is performed on the storage locations to identify the boundaries of the "cut" cell object. A first portion of each identified boundary is identified by background values adjacent to cell object values and a second portion of each boundary is identified by the unique boundary value adjacent to cell object values.

DETAILED DESCRIPTION OF THE PREFERRED EMBODIMENT

As shown in the drawings and described herein, the invention is embodied in a method and apparatus for automatically analyzing "cell objects" which term is used to be generic to cells, portions of cells, such as cell nuclei, and to cell fragments.

The present invention provides tools which enable a human operator of automated cell analysis apparatus to manually modify or affect the cell objects selected for analysis. The particular analysis routine performed on the selected cell objects is not critical to the invention. The embodiment is however described with an analysis routine which measures the perimeter and the area of cells. Those of ordinary skill in the art will appreciate that the tools provided with the present invention can also be used with many other types of analysis routines such as, for example, the analysis of multi-nucleation of cells as disclosed in application Ser. No. 07/645,090 to Bacus, which is hereby incorporated by reference herein.

Figure 1:
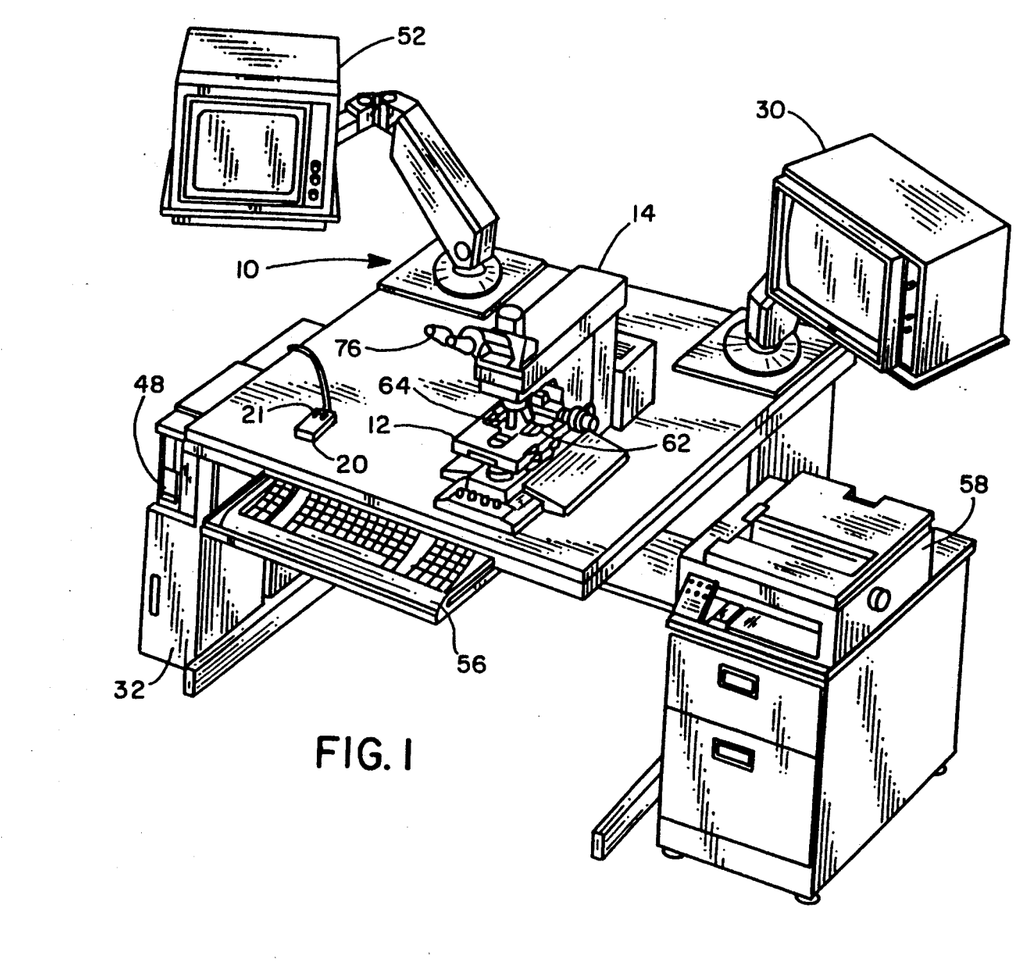
FIG. 1 is an isometric view of an apparatus embodying the invention for analyzing cell samples.

FIG. 1 shows an apparatus embodying the present invention which is generally identified by a numeral 10. Apparatus 10 comprises an optical microscope 12 which may be any conventional type, but in this embodiment is a Reichert Diastar. An optical camera module 14 is mounted on the microscope 12 to enhance optically a magnified image of a cell sample viewed with microscope 12. The optical camera module 14 includes at least one television camera which generates a standard NTSC compatible signal representative of the field of view of microscope 12. An image processo system 28 (FIG. 2) is connected to the camera module 14 to receive the NTSC signal and to store a cell object pixel array in a frame buffer 31 of image processor 28. The image processor 28, which in the preferred embodiment is a Model AT428 from the Data Cube Corporation, is connected to a computer 32 for the processing of the pixel array.

Figure 2:
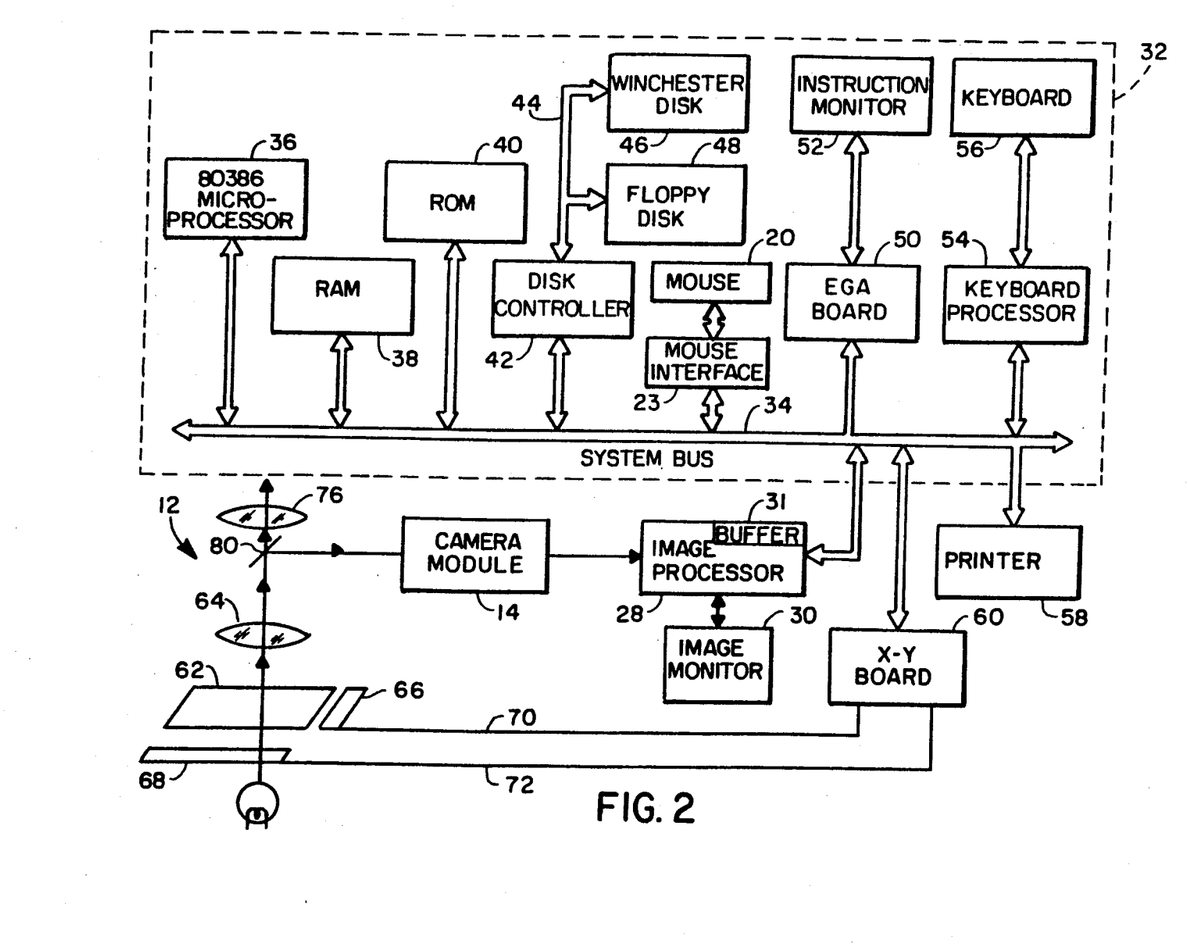
FIG. 2 is a block diagram of the apparatus of FIG. 1.

Computer 32 which is shown in greater detail in FIG. 2 includes a system bus 34 connected to the image processor 28. A microprocessor 36 which in the embodiment is an Intel 80386 is connected to the system bus 34. A random access memory 38 and a read-only memory 40 are also connected to a system bus 34 for the storage and information. A disk controller 42 is connected by a local bus 44 to Winchester disk drive 46 and to a floppy disk drive 48 for secondary information storage. A video conversion board 50, in this embodiment an EGA board having 256K bytes of memory, is connected to the system bus 34 to control an instruction monitor 52 connected to the EGA board 50. A keyboard processor 54 is connected to system bus 34 to interpret signals from a keyboard 56. An interactive computer mouse 20 is also connected to bus 34 via a mouse interface 23. A printer 58 is connected to the system bus 34 for generating paper copies of information generated by computer 32.

An X-Y image field board 60 is connected to the system bus 34 and to a slide holder of the microscope 12 to sense the relative position of slide 62 with respect to a microscope objective 64. Included is a Y position sensor 66 and an X position sensor 68. The Y position sensor 66 is connected via a communication path 70 to the X-Y board 60 and the X position sensor 68 is connected via a communication path 72 to the X-Y board 60. The microscope 12 also includes an eye piece 76, in optical alignment with the objective 64 for the magnification of light forming the image of a cell sample on slide 62.

When using the apparatus 10, a pathologist first collects a cell sample which may be in the form of a tissue section made from frozen or paraffinized prostate tissue. Such a cell sample may include both e s, both of which are referred to as cell objects herein. The cells of the cell sample are placed on slide 62 and fixed thereon. The fixed cell sample is then stained to highlight the cell features to be analyzed. Since the analysis routine of the preferred embodiment measures cell perimeter and area, the stain used is one which highlights the cell cytoplasm for perimeter and area measurement. Eosin-Y is an example of such a stain. When other cell objects or constituents such as nuclear DNA are to be analyzed, other stains may be used to highlight these features.

Figure 4:
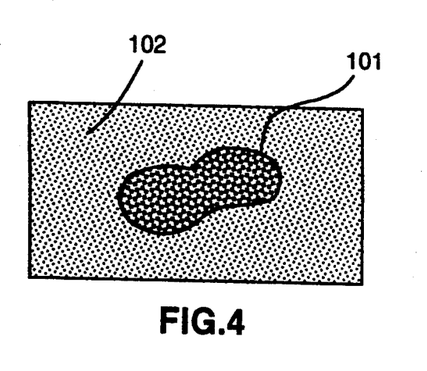
FIGS. 4 through 6 represent cell sample video images and the functions performed with such images for the automatic analysis thereof by the apparatus.

The microscope slide 62 is then placed on the carrying stage of microscope 12 and the objective 64 is focused thereon. A portion of the light from the objective 64 travels through a beam splitting mirror 80 to eye piece 76 where it may be viewed by an observer. The beam splitting mirror 80 conveys the remainder of the light from objective 64 to camera module 14, which generates an NTSC signal representing the image and applies that signal to the image processor 28. Image processor 28 digitizes the image received from camera unit 14 and stores the digitized image in a frame buffer 31 of the image processor. The frame buffer comprises a 256×256 array of image representing storage locations called storage elements, each of which corresponds to one picture element (pixel) of the displayed image. Image processor 28 encodes the gray level of each pixel of the image, and stores that gray level value in the one of the imaging representing storage elements corresponding to the pixel. Thus, after image digitization is completed, the frame buffer contains a 256×256 array of gray level values in which each storage location of the array represents one image pixel. The contents of the frame buffer 31 are presented to an image monitor 30, which displays a field of the cell sample. Also, the storage locations of the frame buffer 31 are within the address spectrum of microprocessor 36 so that the values stored in the storage locations can be readily accessed by the microprocessor over bus 34. FIG. 4 represents an exemplary image which is presented to the apparatus 10 and digitized as above described.

Each storage location of the image array stored in frame buffer 31 stores 8 bits. This permits each storage location to store one of up to 256 unique values. Certain values of the 256 possible values are reserved and not used to represent gray levels. In the preferred embodiment, the values 0 through 229 are used to represent valid gray levels and the values 230 through 255 are reserved for other purposes. Also, the address of each storage location in the array consists of its row and column number. The row and column numbers begin at the upper left corner of the image so that the uppermost and leftmost storage location has an address 0,0.

Figure 3:
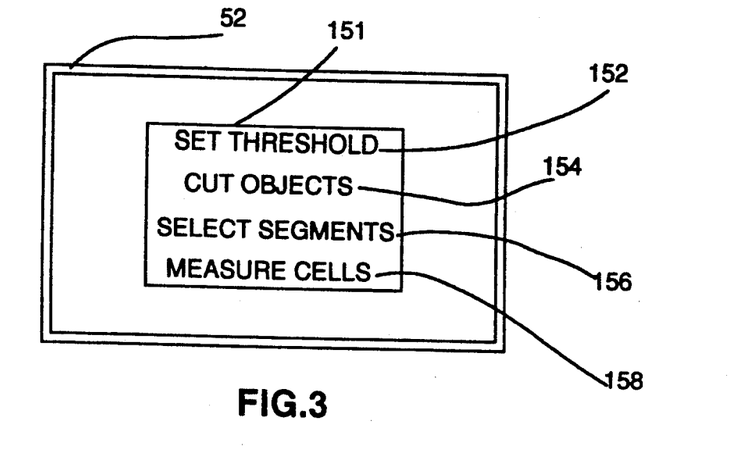
FIG. 3 is a representation of a menu screen of menu items presented to an operator of the apparatus.

When the apparatus 10 is in operation, t he operator has a number of options or functions which can be chosen to acquire and process data from a cell sample. FIG. 3 shows a menu screen 151 displayed to an operator on instruction monitor 52 for the selection of functions to be performed by the apparatus 10. The set threshold option 152 allows the operator to set a gray level threshold which is used by the apparatus 10 to distinguish between cell objects and image background.

The operator enters a threshold value by selecting the set threshold menu item 152 using the mouse 20 then typing a threshold value when prompted on the instruction monitor 52. After the threshold is entered, each of the 256×256 gray level values stored in the frame buffer 31 array is read and compared to the entered threshold value. When the value stored in a given a storage location of the array is less than the threshold value, a predetermined value such as zero, to stored in the given location. Alternatively, when the value stored in a given location is greater than or equal to the entered threshold value, the gray level is left in that storage location. The threshold comparisons and the rewriting of storage locations creates a single array which is used as both a search map and as the image presented to image monitor 30 for display. In the preferred embodiment, the threshold comparison is performed by the microprocessor 36 which first reads the array of values from the frame buffer 31, performs the threshold comparison, modifies selected storage locations of its array and returns the modified array to the frame buffer 31 for display.

Figure 5:
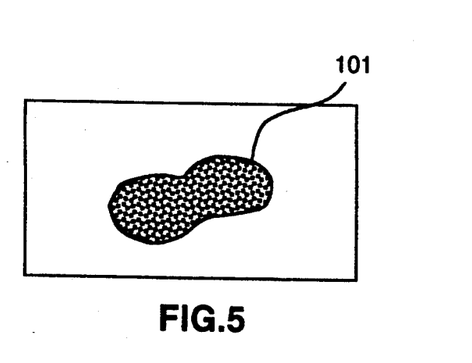
Figure 6:
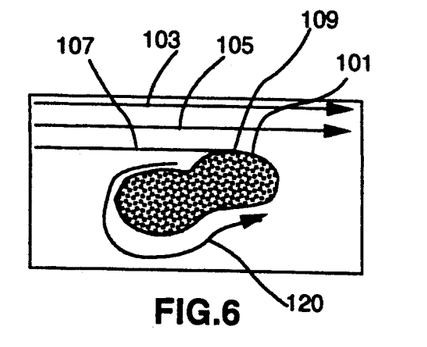

FIG. 4 represents a pre-thresholding cell sample image showing a cell object 101 in an image also comprising significant background clutter 102. In contrast, FIG. 5 represents the image digitally stored in the apparatus 10 and displayed to the operator on monitor 52, after the under threshold array values of FIG. 4 have been set to zero. After the unneeded background information is removed, the cell objects, e.g., 101, are located and their boundaries are recorded. Cell objects are located in a raster scan type image review which is performed by microprocessor 36 on a copy of the frame buffer 31 storage values. First, values are read from the uppermost row of storage locations in the image array and compared with the background value of zero. In FIG. 6, the lines 103 and 105 represent the analysis of such stored information in which all storage locations store the background value. The rows of storage locations are examined in sequence, until a storage location value representing a pixel 109 in scan row 107 is discovered which exceeds the background value. Upon locating the over threshold pixel 109, a boundary search of cell object 101 is begun by microprocessor 36. In the course of the following description, a boundary pixel is one which corresponds to a storage location having a gray level value above the background value and which is immediately adjacent to a pixel corresponding to a storage location having a value equal to the assigned background value, i.e., zero.

Figure 7:
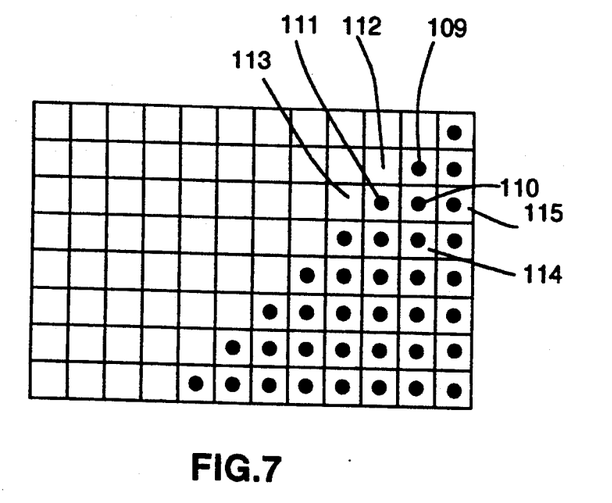
FIG. 7 represents the picture elements of a cell sample video image portion and is discussed with regard to automatic cell object boundary identification.

FIG. 7 represents a contiguous grouping of pixels from the image of FIG. 6 in the vicinity of the first found boundary pixel 109. In FIG. 7, each pixel is represented by a small square, some of which have been assigned a number from 109 through 115. Each pixel corresponding to a storage location having a cell object gray level value, e.g., pixel 109, includes a dot in its center while pixels corresponding to storage locations, e.g., 112, storing the background value are shown without such a dot. The boundary pixels of a cell object, e.g., 101, are identified in a neighbor search which is known in the art and described, for example, in U.S. Pat. Nos. 4,097,845 and 4,199,748 to Bacus. Such neighbor searching to identify boundaries is briefly described below, with regard to FIG. 7 and to FIG. 13, which is a flow diagram of automatic boundary searching.

Figure 13:
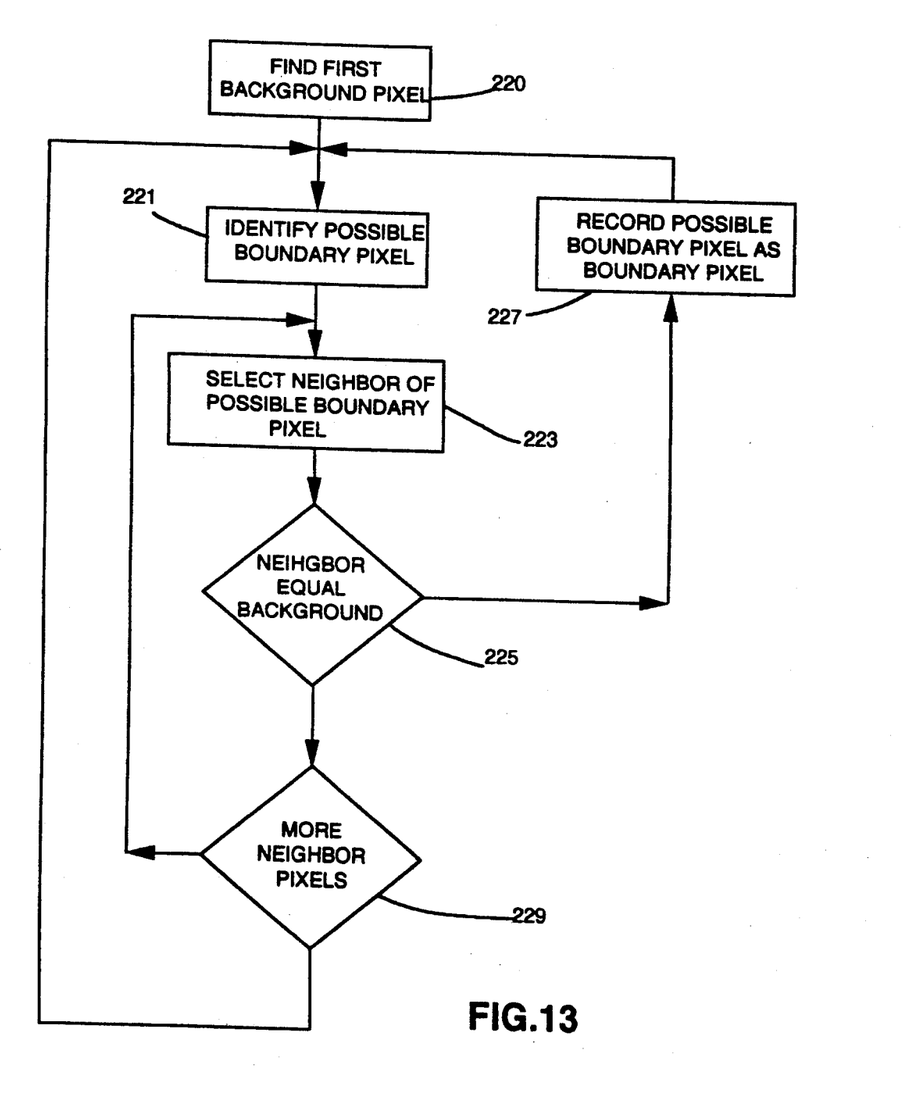
FIG. 13 is a flow diagram of automatic boundary identification.

In FIG. 13, step 220 represents the raster scan search discussed above which identifies pixel 109. After pixel 109 is detected in the raster scan, an immediate neighbor pixel, e.g., 110 to pixel 109 is selected as a possible boundary pixel in a step 221. Upon selection of pixel 110 as a possible boundary pixel, storage locations corresponding to its immediate horizontal and vertical neighbor pixels 109, 111, 114 and 115 are read in a step 223 to determine if they store the background value. The value stored for each of the selected neighbor pixels 109, 111, 114 and 115 is compared in sequence by step 225 to the background value of zero. When a neighbor pixel selected in step 223 corresponds to a stored background value of zero, the possible boundary pixel selected in step 220, is a boundary pixel and its location is recorded in step 227 on a list stored in memory 38 of computer 32. In the present example, none of the pixels 109, 111, 114 or 115 correspond to a storage location storing the background value. The absence of additional neighbor pixels to the selected possible boundary pixel 110 is detected in a step 229 and flow returns to the step 221 where another possible boundary pixel is selected. In the present example, pixel 111 is selected in step 221. Pixels are selected for review in a generally counterclockwise direction around the last selected boundary pixel. Pixel 113 will be selected in step 223 as a neighbor of the newly selected possible boundary pixel 111. When pixel 113 which is an immediate neighbor of possible boundary pixel 111 is identified in step 225 as corresponding to the background value, pixel 111 is selected as a boundary pixel. As before, after boundary pixel 111 is selected and recorded (step 227), its immediate neighbor pixels are checked to identify and record additional boundary pixels. This process continues in a generally counterclockwise direction around the cell object 101, as indicated by arrow 120 (FIG. 6) until the original boundary pixel 109 is again located. Finding pixel 109 in the boundary search, indicates that the entire set of boundary pixels has been found and that the raster scan can continue to find other cell objects in the image.

Figure 18:
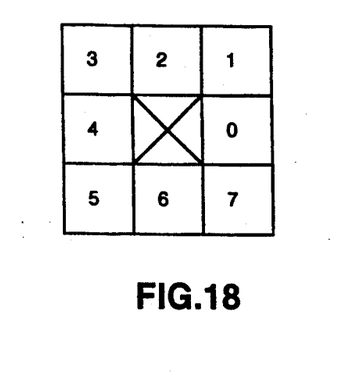
FIG. 18 shows relative pixel position numbers of pixels surrounding a pixel of interest.

In the present embodiment, the location recorded on the boundary pixel list for each boundary pixel is a number from 0 through 7 representing its relative position around the immediately preceding boundary pixel. The relative position values of pixels around a boundary pixel are shown in FIG. 18. A boundary can be identified by starting with the address of the first boundary pixel 109 and proceeding in increments identified by the stored list of relating position numbers. It should be mentioned that the stored location of each pixel could also be its absolute row and column address. Row and column address storage for each pixel would require additional storage space but might provide advantages in certain types of analysis.

After identifying the boundary of cell object 101 image parameter measurement can begin. The operator selects such parameter measurements by using the mouse 20 to select the measure cells item 158 of the menu 151. In the parameter measure mode, the apparatus 10 identifies and counts each pixel within the recorded boundary The cell object area is calculated from the total count by multiplying the count by the known area of one pixel. The cell object perimeter can also be calculated from the recorded boundary pixel information. To calculate the perimeter, each boundary pixel which is horizontally or vertically displaced from its immediately prior boundary pixel is assigned a perimeter value of one, and each boundary pixel which is diagonally displaced from its immediately prior boundary pixel is assigned a perimeter value of the square root of two. The perimeter values of all boundary pixels are then added together and the result of the addition is multiplied by the length of one pixel side to yield the cell object perimeter.

Figure 8:
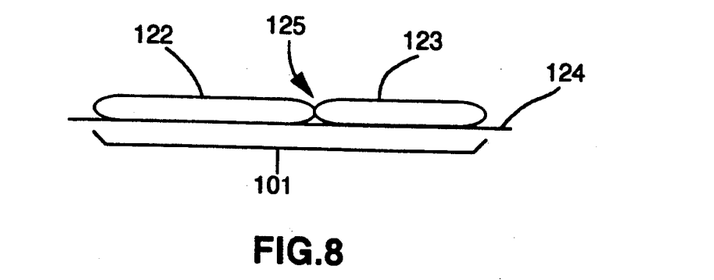
FIG. 8 is a side plan view of a two cell object combination which yields a top image as shown in FIGS. 4 through 6 and 9 through 11.

The preceding cell object boundary identification method provides satisfactory results in most situations. However, in certain situations, it is desirable to be able to split an apparently single cell object into two or more cell objects before analysis. FIG. 8 which represents a side edge view of the image of cell object 101, shows one situation where cell object splitting is desirable. In FIG. 8, it is apparent that cell object 101 actually comprises two cells 122 and 123 lying on a substrate 124. Cells 122 and 123 are in contact at a point shown at 125. Since the cells 122 and 123 are in contact, no background is optically apparent between them and the apparatus 10 operating as described above will analyze their combination as the single cell object 101.

Figure 9:
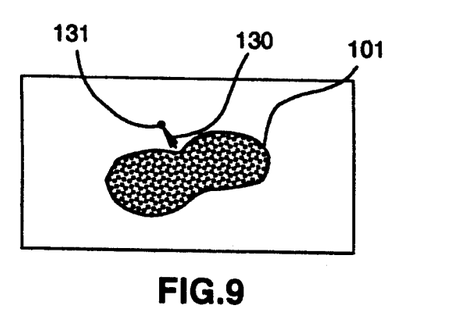
FIGS. 9 through 11 represent cell sample video images and the functions performed with such images in operator controlled cell object boundary identification.
Figure 10:
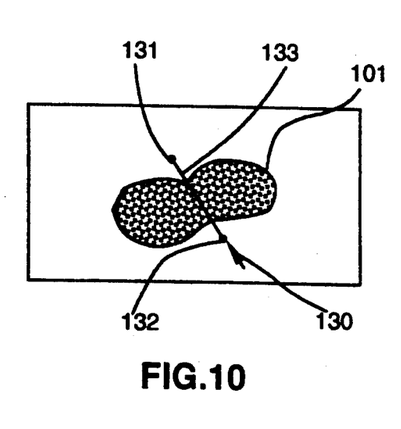

When an operator views the image on monitor 30, subtle variation in displayed gray level or other visible clues may indicate that what appears to the previously described perimeter search routine as a single cell object, is actually two cell objects as shown in FIG. 8. The operator can then select the cut objects item 154 from menu 151 (FIG. 3) to separate the objects 122 and 123 into two regions for analysis. In the cut object mode, a mouse cursor 130 (FIG. 9) is visible on the image monitor 30, which can be moved about the image in the known manner by moving the mouse 20. To split cell object for analysis purposes, the operator clicks a mouse button 21 at a starting point 131 in the background portion of the displayed image. After selecting starting point 131, the mouse cursor 130 can be moved and a line 133 is displayed connecting the cursor to the selected starting point 131. FIG. 10 represents a line 133 which is displayed between the starting point 131 and mouse cursor 130. When the mouse cursor 130 is again in image background at an end point 132, the displayed line 133 defines the line along which the cell object is to be separated. The mouse button 21 is again pressed to define the end point 132 for the separation line 133.

When the termination point 132 of line 133 is selected, the storage locations of the array in buffer 31 corresponding to the pixels transversed by the line 133, are changed to store a value which is unique to operator drawn boundary lines. As previously discussed, each of the array storage locations can store values from zero through 255, but no values greater than 229 are used to store gray levels or background. In the preferred embodiment, the number 250 is stored in each image array storage location corresponding to the line 133. The number 250 is stored in the array only to denote an operator defined cell object boundary.

Figure 14:
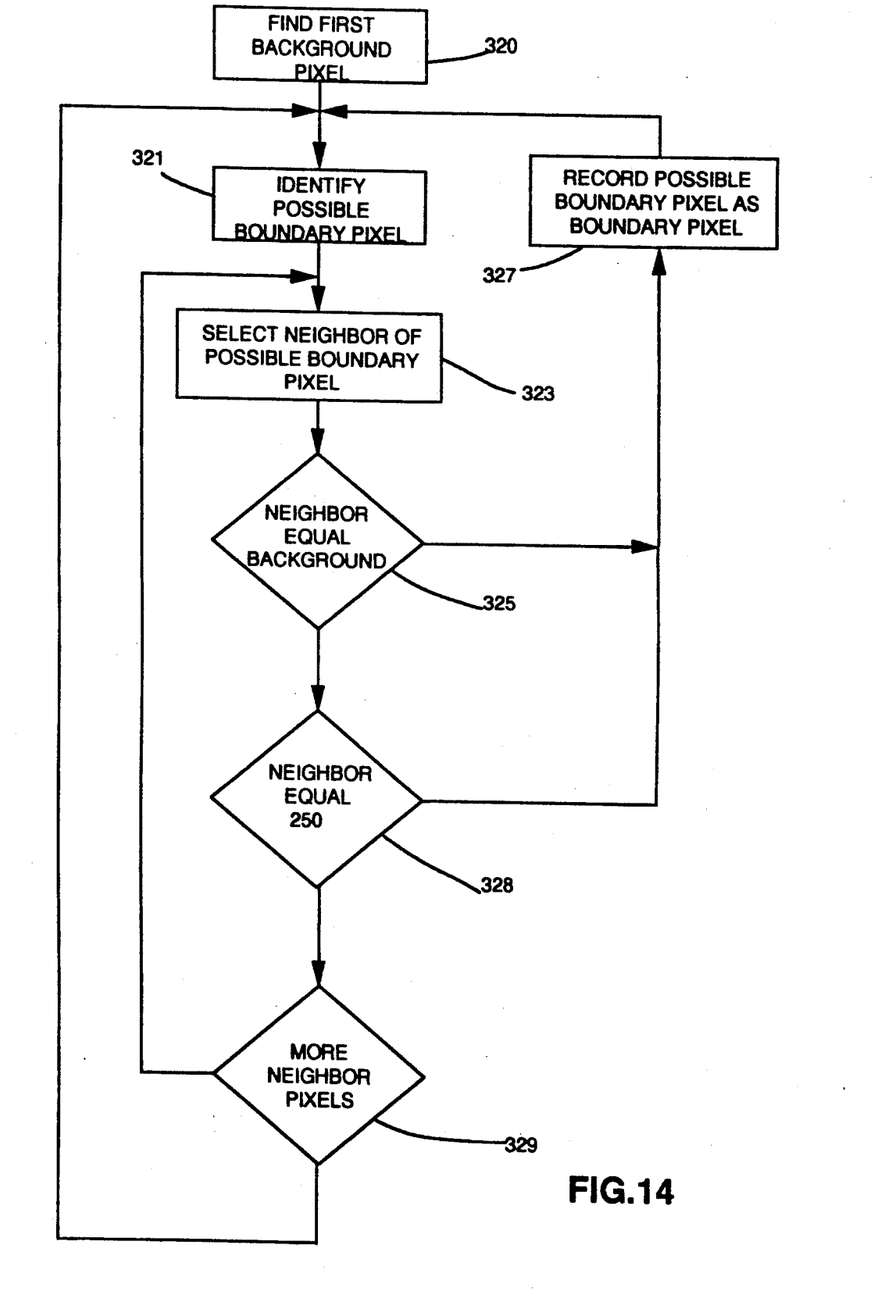
FIG. 14 is a flow diagram of boundary identification with an operator marked boundary portion.

After the drawn line 133 is selected by the operator, the apparatus 10 performs a cut object boundary search routine as shown in FIG. 14. As with the background threshold comparison, the boundary search routine of FIG. 14 is performed by microprocessor 36 on a copy of the storage location values read from frame buffer 31 over bus 34. The boundary search routine begins with a raster scan as described with regard to FIG. 6, to find the first boundary pixel 109 of the cell object. The boundary search routine (FIG. 14) is performed on the cell object 101 in a similar manner to that previously described with regard to FIG. 13 except that a pixel is interpreted as a boundary pixel, if it has a neighbor pixel which is either zero representing background or 250 representing the operator drawn separation line 133. The boundary search routine of FIG. 14 is similar to the boundary search routine of FIG. 13, and a function block in FIG. 14 which performs substantially the same function as a block in FIG. 13 is denoted with a numeral having the same tens and units digits. However, with the search of FIG. 14, when a neighbor of a possible boundary pixel is found in step 325 to not equal the background, that neighbor is compared in a step 328 with the unique boundary line value 250. When the neighbor has a storage location value equal to 250, the possible boundary pixel from step 321 is determined to be a boundary pixel and is recorded in step 327. Alternatively, if the neighbor pixel checked in step 328 is not equal to the unique boundary line value 250, then the flow continues to check another neighbor in step 323.

As before, when no more neighbors exist, step 329 returns the flow to step 321 where another possible boundary pixel is chosen for comparison.

Figure 11:
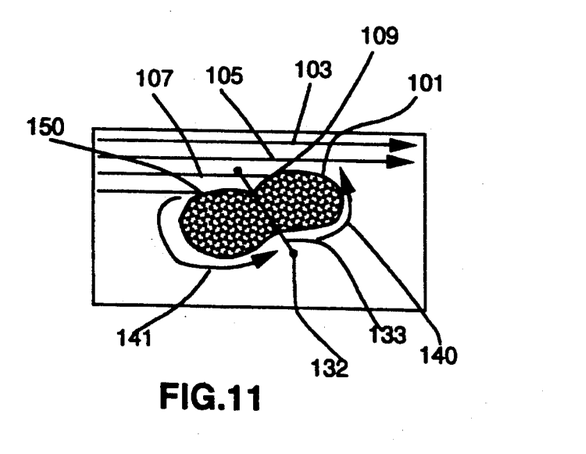
Figure 12:
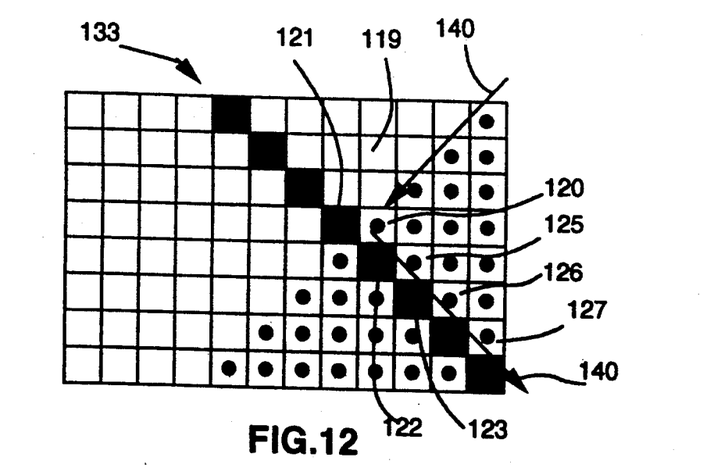
FIG. 12 represents the picture elements of a cell sample video image portion and is discussed with regard to operator controlled boundary identification.

FIG. 12 represents a portion of the stored image array in the vicinity of line 133 through cell object 101. In FIG. 12, background pixels, e.g., 119, are blank, cell object pixels, e.g., 120, include a centered dot, and line 133 identifying pixels, e.g., 121 and 122, are represented by an entirely filled (blackened) pixel area. The boundary search routine proceeds to identify and record pixels in a generally counterclockwise direction, as represented by line segments 140 (FIGS. 11 and 12). When boundary pixel 120 is selected in step 321 as a possible boundary pixel, its neighbor pixel 121 will be checked to determine if it is a background pixel (step 325) or a drawn line pixel (step 328). When the value 250 is found in the storage location corresponding to pixel 121 (step 328), possible boundary pixel 120 will be determined to be a boundary pixel and its location will be recorded in step 327. The boundary search then continues along line segment 140 in parallel with the line defined by pixels 121, 122 and 123, which represent points along line 133. Thus, the boundary search proceeds from pixel 109 along line 140 until a pixel corresponding to a storage location having a value 250 indicating that it is part of line 133 is found. The boundary search routine, treats the value of 250, the same as a background pixel and follows the pixels, e.g., 121 and 122, of line 133 through the cell object 101. When background pixels are again identified at the exit of line 133 from cell object 101 (FIG. 11), the boundary search routine follows the boundary in a counterclockwise direction back to the start pixel 109. At the completion of the boundary search routine for cell object 123, the raster scan begins again until the boundary of cell object 122 is discovered at a pixel 150 (FIG. 11). Upon finding boundary pixel 150, the boundary routine as shown in FIG. 14 is performed again along a path generally shown as 141. The latter boundary search results in a second boundary pixel list for cell object 122. The two boundary pixel lists representing cell objects 122 and 123 can then be used in an analysis routine to determine the areas and perimeters of the two cell objects. The line 133 drawn to separate the cell object 101 in the preceding example was a straight line. It will be apparent that the search routine of FIG. 14 will also follow curved or other shaped lines which pass through a cell object.

Figure 15:
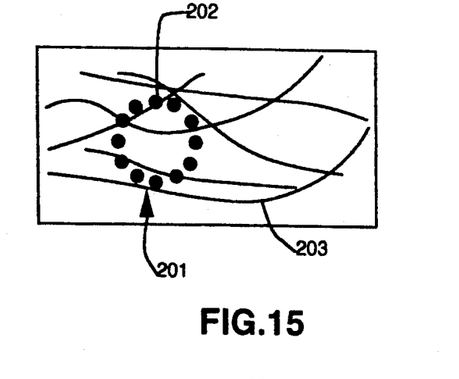
FIGS. 15 through 17 represent a video image of a cell sample undergoing an operator controlled procedure to isolate a portion of the cell sample for analysis.

FIG. 15 represents another cell sample representing image which is difficult to analyze by prior automated techniques. The image of FIG. 15 includes a cluster or nodule 201 of cell objects 202 on a background of fibrous strands 203. The density and intersections of the strands 203 are such that the previously described background thresholding cannot remove them from the image. Accordingly, isolation of cluster 201 for review is difficult. The boundary line drawing capability of the present invention, however, can be used to isolate regions of interest in a cell object image of the type shown in FIG. 15.

Figure 16:
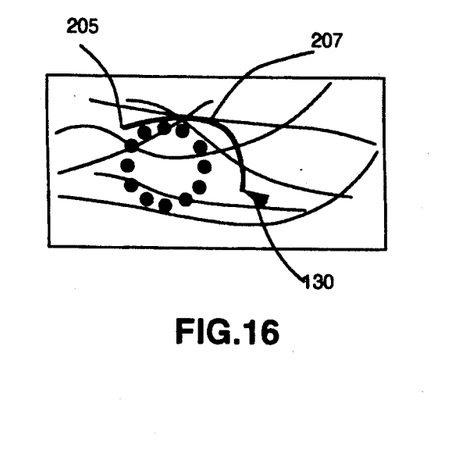
Figure 17:
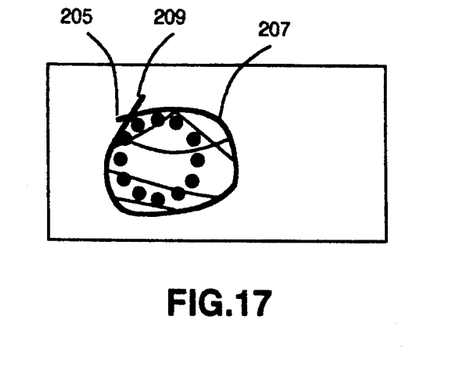

Regions of interest are isolated with the apparatus 10 by first selecting the select segment item 156 from menu 151 (FIG. 3). The select segments mode of operation enables the drawing of a boundary line around a region of interest in an image and deleting all parts of the image outside of the boundary line. When in the select segment mode, the mouse cursor 130 appears on the image monitor 30. The mouse 20 is then manipulated to move the cursor to a point near the object of interest and the mouse button 21 is pressed to mark a starting point 205. After pressing the button 21, a line 207 (FIG. 16) starting at the initial selection point 205 is drawn by moving the mouse cursor 130. To select a region of interest, the line is drawn completely around the region and across itself as shown in FIG. 17. Mouse button 21 is again pressed at a point 209 (FIG. 17) to stop line drawing after the lines cross. As in the cell cutting mode, the storage locations corresponding to the pixels of the line 207 are changed to a unique boundary indicating value. The unique value is the number 250 as in the cell cutting mode.

After the endpoint 209 of line 207 is selected, a select segment search routine is started to identify the boundary defined by line 207. The select segment search routine begins with a raster scan of the storage locations in the frame buffer 31 and continues row by row until a first storage locations storing the unique value 250 is identified. Upon finding the first uniquely valued storage location, a boundary search routine is begun which records in the memory 38 of computer 32a list of the row and column addresses of each storage location storing the value 250. The boundary search consists of searching the neighbor storage locations of each boundary storage location until a neighbor storing the value 250 is discovered. Then the neighbors of the newly found boundary storage location are searched for the value 250, as before.

After the array storage locations of the boundary line 207 are identified, they are used to set all pixels outside the boundary to the background level. This isolates the region of interest inside the boundary and an analysis routine can be performed.

The description of the preceding embodiment includes a step of comparing pixel values to a cell object gray level threshold and modifying the storage locations in the frame buffer 31 by setting storage locations less than the cell object gray level threshold to a background level of zero. The present invention can also be used without such pre-thresholding and value modifying. When the background representing pixels of the frame buffer 31 are not pre-set to a background value, step 225 of FIG. 13 and step 325 of FIG. 14 are changed to a comparison between the value of a neighbor pixel and the cell object gray level threshold. When the value of a neighbor pixel is less than the cell object gray level value indicating that it is a background pixel, the flow proceeds to the record step 227 in FIG. 13 or to the record step 327 in FIG. 14. Alternatively, when the value of a neighbor pixel is greater than or equal to the cell object gray level threshold indicating that it is not a background pixel, the flow proceeds to the step 229 in FIG. 13 or to the step 328 in FIG. 14.

While a preferred embodiment of the invention has been illustrated, it will be obvious to those skilled in the art that various modifications and changes may be made thereto without departing from the scope of the invention as defined in the appended claims. Then the neighbors of the newly found boundary storage location are searched for the value 250, as before.

After the array storage locations of the boundary line 207 are identified, they are used to set all pixels outside the boundary to the background level. This isolates the region of interest inside the boundary and an analysis routine can be performed.

The description of the preceding embodiment includes a step of comparing pixel values to a cell object gray level threshold and modifying the storage locations in the frame buffer 31 by setting storage locations less than the cell object gray level threshold to a background level of zero. The present invention can also be used without such pre-thresholding and value modifying. When the background representing pixels of the frame buffer 31 are not pre-set to a background value, step 225 of FIG. 13 and step 325 of FIG. 14 are changed to a comparison between the value of a neighbor pixel and the cell object gray level threshold. When the value of a neighbor pixel is less than the cell object gray level value indicating that it is a background pixel, the flow proceeds to the record step 227 in FIG. 13 or to the record step 327 in FIG. 14. Alternatively, when the value of a neighbor pixel is greater than or equal to the cell object gray level threshold indicating that it is not a background pixel, the flow proceeds to the step 229 in FIG. 13 or to the step 328 in FIG. 14.

While a preferred embodiment of the invention has been illustrated, it will be obvious to those skilled in the art that various modifications and changes may be made thereto without departing from the scope of the invention as defined in the appended claims.

What is claimed is:

1. In a cell analysis apparatus, a method of analyzing, with a predetermined analysis routine, an image of a cell sample including at least one cell object surrounded by image background, said method comprising:

creating a search mask of said cell sample image by storing image representing picture element values in a plurality of storage locations;

displaying a representation of said cell sample to an operator;

assigning a unique boundary value to selected ones of said storage locations of said picture element values stored in said search mask at storage locations selected by an operator in a line from said image background through said at least one cell object and returning to said image background;

identifying at least one boundary of a region of said cell sample image by a search routine in which said unique value is recognized as being a region boundary; and analyzing by said analysis routine the regions delimited by said at least one boundary identified in said identifying step.

2. A method in accordance with claim 1 wherein said displayed representation comprises a plurality of picture elements each corresponding to one of said search mask storage locations and said assigning step comprises:

drawing at least one line on said displayed representation; and assigning said unique value to the ones of said search mask storage locations corresponding to ones of said picture elements making up said at least one line.

3. A method in accordance with claim 1 wherein said search mask creating step comprises storing a gray level picture element representation of said cell sample image and said displaying step comprises displaying said search mask on a video monitor.

4. In a cell analysis apparatus comprising a storage array having a plurality of storage locations for storing values, a method of analyzing a cell sample including at least one cell object on a background, said method comprising:

producing an optical image of said cell sample;

separating said optical image into a plurality of picture elements each representing a portion of said optical image and storing in each of said storage locations a gray level value representing one picture element of said optical image;

storing a predetermined background value in each of said storage locations corresponding to a background picture element;

displaying on a video monitor a video image generated from said values stored in said storage locations;

storing a unique boundary value in ones of said storage locations selected by an operator of said apparatus, said storing boundary value step comprising, selecting by means of a moveable cursor a line starting point in a first background portion of said displayed video image, moving said cursor to trace a line across a cell object portion of said displayed video image, selecting an ending point for said line in a background portion of said displayed video image;

identifying from the values stored by said storage locations at least one boundary derived from said stored predetermined background values and said stored unique boundary values; and analyzing a portion of said cell sample within said at least one boundary.

5. A method in accordance with claim 4 wherein said predetermined background value storing step comprises:

comparing the value of each storage location to a predetermined cell object threshold value to identify storage locations corresponding to picture elements representing optical image background; and changing the value stored by each storage location identified in said comparing step to the predetermined background value.

6. A method in accordance with claim 4 comprising storing said unique boundary value in ones of said storage locations corresponding to picture elements traversed by said line.

7. In a cell analysis apparatus comprising a storage array having a plurality of storage locations for storing values, a method of analyzing a cell sample including at least one cell object on a background, said method comprising:

producing an optical image of said cell sample;

separating said optical image into a plurality of picture elements each representing a portion of said optical image and storing in each of said storage locations a gray level value representing one picture element of said optical image;

storing a predetermined background value in each of said storage locations corresponding to a background picture element;

displaying on a video monitor a video image generated from said values stored in said storage locations;

storing a unique boundary value in ones of said storage locations corresponding to the picture elements of a line drawn at the direction of an operator on said video image, said line extending through an image of said cell object from background to background;

performing a raster search of said storage locations to identify a first storage location storing a gray level value corresponding to a cell object picture element;

performing a neighbor search from said first storage location to identify a boundary delimiting a portion of said cell object, said boundary being defined by storage locations storing said unique boundary value and by storage locations storing said predetermined background value; and analyzing said portion of said cell sample within said boundary.

8. In an automated analysis apparatus a method of analyzing a cell sample comprising at least one cell object, said method comprising:

displaying on a video monitor a video image of said cell sample;

drawing a line through said at least one cell object in said video image by an operator;

selecting by said apparatus a cell object portion of said cell object for analysis, at least one portion of a boundary of said selected cell object portion being defined by said line; and analyzing said selected cell object portion by said apparatus in accordance with a predetermined analysis routine.

9. A method in accordance with claim 8 wherein said drawing step comprises:

manipulating a computer pointing device to move an image cursor across said cell object; and drawing on said monitor a line along a path defined by the image cursor.

10. A method in accordance with claim 8 comprising:

separating an optical image of said cell sample into a plurality of picture elements each representing a portion of said optical image and storing in each of a plurality of storage locations a gray level value representing one picture element of said optical image;

storing, responsive to said drawing step a unique boundary signifying value in ones of said storage locations defined by the position of said line on said at least one cell object; and said selecting step comprises identifying ones of said storage locations storing said unique boundary signifying value.

11. Apparatus for analyzing a cell sample comprising at least one cell object, said apparatus comprising:

means for displaying a video image of said cell sample;

means for drawing a line through said at least one cell object on said video image;

means for selecting a cell object portion of said at least one cell object for analysis, at least one boundary of said selected cell object portion being defined by said line drawn on said video image; and means for analyzing said selected cell object portion in accordance with a predetermined analysis routine.

* * * * *